(12) United States Patent
Fine et al.

(10) Patent No.: US 10,926,054 B2
(45) Date of Patent: Feb. 23, 2021

(54) SYSTEMS AND DEVICES FOR GENERATING NITRIC OXIDE

(71) Applicant: VERO BIOTECH LLC, Atlanta, GA (US)

(72) Inventors: David H. Fine, Cocoa Beach, FL (US);
Bryan Johnson, Orlando, FL (US);
Gregory Vasquez, Cocoa, FL (US)

(73) Assignee: Vero Biotech LLC, Atlanta, GA (US)

(*) Notice: Subject to any disclaimer, the term of this patent is extended or adjusted under 35 U.S.C. 154(b) by 0 days.

(21) Appl. No.: 15/469,447

(22) Filed: Mar. 24, 2017

(65) Prior Publication Data

US 2017/0259025 A1  Sep. 14, 2017

Related U.S. Application Data

(63) Continuation of application No. 14/612,266, filed on Feb. 2, 2015, now Pat. No. 9,604,028, which is a
(Continued)

(51) Int. Cl.
*A61M 16/12* (2006.01)
*A61M 16/10* (2006.01)
(Continued)

(52) U.S. Cl.
CPC ............ *A61M 16/12* (2013.01); *A61M 16/10* (2013.01); *A61M 16/104* (2013.01);
(Continued)

(58) Field of Classification Search
CPC .. A61M 16/00; A61M 16/0093; A61M 16/10; A61M 16/105; A61M 16/106;
(Continued)

(56) References Cited

U.S. PATENT DOCUMENTS

| | | |
|---|---|---|
| 1,021,234 A | 3/1912 | Von Berneck |
| 2,272,810 A | 2/1942 | Denys |

(Continued)

FOREIGN PATENT DOCUMENTS

| | | |
|---|---|---|
| DE | 4419860 A1 | 12/1995 |
| DE | 19612289 A1 | 10/1997 |

(Continued)

OTHER PUBLICATIONS

Examination Report No. 1 for Australian Application No. 2009282986, dated Dec. 15, 2014, 3 pages.
(Continued)

*Primary Examiner* — Colin W Stuart

(57) ABSTRACT

Various systems and devices for generating nitric oxide are disclosed herein. According to one embodiment, the device includes a body having an inlet, an outlet, and a porous solid matrix positioned with the body. The porous solid matrix is coated with an aqueous solution of an antioxidant, wherein the inlet is configured to receive a gas flow and fluidly communicate the gas flow to the outlet through the solid matrix to convert nitrogen dioxide in the gas flow into nitric oxide. The porous solid matrix allows the device to be used in any orientation. Additionally, the porous solid matrix provides a rigid structure suitable to withstand vibrations and abuse without compromising device functionality.

10 Claims, 2 Drawing Sheets

Related U.S. Application Data continuation of application No. 14/107,554, filed on Dec. 16, 2013, now Pat. No. 8,944,049, which is a continuation of application No. 12/541,137, filed on Aug. 13, 2009, now Pat. No. 8,607,785.

(60) Provisional application No. 61/090,614, filed on Aug. 21, 2008.

(51) Int. Cl.
  *A62B 7/08* (2006.01)
  *A62B 21/00* (2006.01)
  *A61M 16/16* (2006.01)

(52) U.S. Cl.
  CPC ........ *A61M 16/107* (2014.02); *A61M 16/109* (2014.02); *A61M 16/1075* (2013.01); *A61M 16/16* (2013.01); *A62B 7/08* (2013.01); *A62B 21/00* (2013.01); *A61M 2202/0275* (2013.01)

(58) Field of Classification Search
  CPC ................ A61M 16/107; A61M 16/12; A61M 16/1075; A61M 16/16; A61M 16/122; A61M 16/125; A62B 7/08; A62B 7/10; A62B 19/02; A62B 19/00
  USPC .................................................. 128/202.26
  See application file for complete search history.

(56) References Cited

U.S. PATENT DOCUMENTS

| | | | |
|---|---|---|---|
| 3,930,813 | A | 1/1976 | Gessner |
| 4,010,897 | A | 3/1977 | Treharne |
| 4,270,933 | A * | 6/1981 | Meny ..................... B01D 39/14 55/524 |
| 4,287,040 | A | 9/1981 | Alamaro |
| 4,399,942 | A | 8/1983 | Chand |
| 4,774,069 | A | 9/1988 | Handley |
| 4,778,450 | A | 10/1988 | Kamen |
| 4,963,327 | A | 10/1990 | Russell |
| 5,228,434 | A | 7/1993 | Fishman |
| 5,396,882 | A | 3/1995 | Zapol |
| 5,485,827 | A | 1/1996 | Zapol |
| 5,514,204 | A | 5/1996 | Sheu et al. |
| 5,525,357 | A | 6/1996 | Keefer |
| 5,545,614 | A | 8/1996 | Stamler |
| 5,558,083 | A | 9/1996 | Bathe |
| 5,570,683 | A | 11/1996 | Zapol |
| 5,615,669 | A | 4/1997 | Olsson |
| 5,647,354 | A | 7/1997 | Lakhani et al. |
| 5,651,358 | A | 7/1997 | Briend |
| 5,676,963 | A | 10/1997 | Keefer |
| 5,683,668 | A | 11/1997 | Hrabie |
| 5,692,495 | A | 12/1997 | Sheu |
| 5,823,180 | A | 10/1998 | Zapol |
| 5,827,420 | A | 10/1998 | Shirazi |
| 5,839,433 | A | 11/1998 | Higenbottam |
| 5,846,297 | A | 12/1998 | Schleicher et al. |
| 5,871,009 | A | 2/1999 | Rydgren |
| 5,873,359 | A | 2/1999 | Zapol |
| 5,994,444 | A | 11/1999 | Trescony |
| 6,046,383 | A | 4/2000 | Elsenga-Boersma et al. |
| 6,103,275 | A | 8/2000 | Seitz et al. |
| 6,109,260 | A | 8/2000 | Bathe |
| 6,116,235 | A | 9/2000 | Walters et al. |
| 6,158,432 | A | 12/2000 | Biondi et al. |
| 6,158,434 | A | 12/2000 | Lugtigheid |
| 6,190,704 | B1 | 2/2001 | Murrell |
| 6,261,594 | B1 | 7/2001 | Smith |
| 6,270,779 | B1 | 8/2001 | Fitzhugh |
| 6,576,044 | B1 | 6/2003 | Ho et al. |
| 6,584,972 | B2 | 7/2003 | McPhee |
| 6,635,273 | B1 | 10/2003 | Loscalzo et al. |
| 6,749,834 | B2 | 6/2004 | Fein et al. |
| 6,758,214 | B2 | 7/2004 | Fine et al. |
| 6,896,899 | B2 | 5/2005 | Demopolos et al. |
| 6,957,652 | B2 | 10/2005 | Matsuoka |
| 7,025,869 | B2 | 4/2006 | Fine et al. |
| 7,040,313 | B2 | 5/2006 | Fine et al. |
| 7,045,106 | B2 | 5/2006 | Takahashi et al. |
| 7,166,139 | B2 | 1/2007 | Wunning |
| 7,282,519 | B2 | 10/2007 | Garvey et al. |
| 7,288,664 | B2 | 10/2007 | Kleiner |
| 7,407,632 | B2 | 8/2008 | Ross |
| 7,618,594 | B2 | 11/2009 | Rounbehler |
| 8,607,785 | B2 | 12/2013 | Fine |
| 8,701,657 | B2 | 4/2014 | Fine |
| 8,944,049 | B2 | 2/2015 | Fine |
| 9,604,028 | B2 | 3/2017 | Fine et al. |
| 2001/0012851 | A1 | 8/2001 | Lundy |
| 2002/0090401 | A1 | 7/2002 | Tucker et al. |
| 2002/0129815 | A1 | 9/2002 | McPhee |
| 2003/0136405 | A1 * | 7/2003 | Goede ............... A61M 15/0065 128/203.12 |
| 2005/0072427 | A1 | 4/2005 | Matsuoka |
| 2005/0142218 | A1 | 6/2005 | Tucker et al. |
| 2005/0215991 | A1 | 9/2005 | Altman et al. |
| 2005/0217668 | A1 | 10/2005 | Figley et al. |
| 2006/0048779 | A1 | 3/2006 | Rounbehler et al. |
| 2006/0153888 | A1 | 7/2006 | Leverett et al. |
| 2006/0180147 | A1 | 8/2006 | Rounbehler |
| 2007/0062532 | A1 | 3/2007 | Choncholas |
| 2007/0215147 | A1 * | 9/2007 | Ho ........................ A61M 16/08 128/200.24 |
| 2011/0168174 | A1 | 7/2011 | Fine et al. |

FOREIGN PATENT DOCUMENTS

| | | |
|---|---|---|
| EP | 0533409 A1 | 3/1993 |
| EP | 1323468 A1 | 7/2003 |
| JP | H08-47534 A | 2/1996 |
| JP | 2004-065636 A | 3/2004 |
| JP | 2008-510675 A | 4/2008 |
| WO | WO 1994/016740 | 8/1994 |
| WO | WO 1995/007610 | 3/1995 |
| WO | WO 2001/015738 | 3/2001 |
| WO | WO 2002/085785 | 10/2002 |
| WO | WO 2006/023616 | 3/2006 |
| WO | WO 2010/021942 | 2/2010 |

OTHER PUBLICATIONS

Extended European Search Report for European Application No. 09808647.3, dated Feb. 3, 2014, 6 pages.

Notice of Reasons for Refusal of Japanese Application No. 2011-523891, dated Jul. 24, 2013, 8 pages.

Notice of Reasons for Refusal of Japanese Application No. 2014-085194, dated Mar. 11, 2015, 8 pages.

International Search Report and Written Opinion for International Application No. PCT/US2009/053946, dated Oct. 19, 2009, 6 pages.

Cooney et al., "Products of γ-tocopherol with NO2 and their formation in rat insulinoma (RINm5F) cells," Free Radical Biology and Medicine, vol. 19, Issue 3, Sep. 1995, pp. 259-269.

Licht, W.R. et al., "Use of Ascorbic Acid to Inhibit Nitrosation: Kinetic and Mass Transfer Considerations for an in Vitro System," Carcinogenesis, IRL Press at Oxford University Press, Oxford, Mar. 1988, pp. 365-371.

Mascarenhas, O. C., "Epoxy-Based Medical Grade Adhesive Hydrogels and Nitric Oxide Releasing Poymers", Dissertation Abstracts International, vol. 55/02-B, pp. 445 (1993).

Material Safety Data Sheet, Silica gel, grade 41, 3-8 mesh MSDS, Oct. 9, 2005.

Pulfer, S. K., "Nitric Oxide Releasing Polymers and Their Application to Vascular Devices (Polyethyleneimine, Polytetrafluoroethylene)", Dissertaion Abstracts International, vol. 56/12-B, pp. 6727 (1995).

Roselle, D. C. et al., "Characterization and Nitric Oxide Release Studies of Lipophilic 1-Substituted Diazen-l-ium,1,2-Diolates", Journal of Controlled Release, vol. 51, pp. 131-142 (1998).

(56) References Cited

OTHER PUBLICATIONS

Smith, D. J. et al., "Nitric Oxide-Releasing Polymers Containing the [N(O)NO] Group", Journal of Medicinal Chemistry, vol. 39, No. 5, pp. 1148-1156 (1996).

Suzuki, "Nitrogen Oxides Generation Method for Recovered Nitric Acid by Electrolysis. An Action Plan for Reduction of Low-Level-Liquid-Waste in Processing Plant," Kyoto Daigaku Genshiro Jikkensho, (Tech. Rep.) 1991, Kurri-Ter-361, pp. 19-26.

Taira, M. et al. "Continuous Generation System for Low-Concentration Gaseous Nitrous Acid", Analytical Chemistry, vol. 62, No. 6, pp. 630-633, (1990). International Search Report, 8 pages, Mar. 10, 2004.

Tannenbaum, S.R. et al., "Inhibition of Nitrosamine Formation by Ascorbic Acid," The American Journal of Clinical Nutrition, American Society of Clinical Nutrition, Bethesda, Maryland, Jan. 1991, vol. 53, pp. 247-250.

\* cited by examiner

SYSTEMS AND DEVICES FOR GENERATING NITRIC OXIDE

CLAIM OF PRIORITY

This application is a Continuation of U.S. patent application Ser. No. 14/612,266, filed Feb. 2, 2015, now U.S. Pat. No. 9,604,028, which is a Continuation of U.S. patent application Ser. No. 14/107,554, filed on Dec. 16, 2013, now U.S. Pat. No. 8,944,049, which is a Continuation of U.S. patent application Ser. No. 12/541,137, filed on Aug. 13, 2009, now U.S. Pat. No. 8,607,785, which claims the benefit of U.S. Provisional Application No. 61/090,614, filed Aug. 21, 2008, each of which is incorporated by reference in its entirety.

TECHNICAL FIELD

This description relates to systems and devices for generating nitric oxide.

BACKGROUND

Nitric oxide (NO), also known as nitrosyl radical, is a free radical that is an important signaling molecule. For example, NO causes smooth muscles in blood vessels to relax, thereby resulting in vasodilation and increased blood flow through the blood vessel. These effects are limited to small biological regions since NO is highly reactive with a lifetime of a few seconds and is quickly metabolized in the body.

Typically, NO gas is supplied in a bottled gaseous form diluted in nitrogen gas ($N_2$). Great care has to be taken to prevent the presence of even trace amounts of oxygen ($O_2$) in the tank of NO gas because NO, in the presence of $O_2$, is oxidized into nitrogen dioxide ($NO_2$). Unlike NO, the part per million levels of $NO_2$ gas is highly toxic if inhaled and can form nitric and nitrous acid in the lungs.

SUMMARY

Briefly, and in general terms, various embodiments are directed to systems and devices for generating nitric oxide (NO). According to one embodiment, the device includes a body having an inlet, an outlet, and a porous solid matrix positioned with the body. In one embodiment, the porous solid matrix is made of a silica gel and a thermoplastic resin. The porous solid matrix is coated with an aqueous solution of an antioxidant, wherein the inlet is configured to receive a gas flow and fluidly communicate the gas flow to the outlet through the porous solid matrix to convert nitrogen dioxide in the gas flow into nitric oxide. The porous solid matrix allows the device to be used in any orientation. The porous solid matrix also provides a rigid structure suitable to withstand vibrations and abuse associated with shipping and handling.

In addition to NO-generating devices, various systems for generating and delivering NO to a patient are disclosed herein. According to one embodiment, the system includes a gas source including nitrogen dioxide ($NO_2$), dinitrogen tetraoxide ($N_2O_4$), or NO. The gas source is in communication with a first NO conversion device. The NO conversion device includes an inlet, an outlet, and a solid matrix coated with an aqueous solution of an antioxidant positioned between the inlet and the outlet. The inlet of the NO conversion device is configured to receive a gas flow from the source and fluidly communicate the gas flow through the porous solid matrix to the outlet in order to convert $NO_2$ in the gas flow into NO. The system also includes a patient interface coupled to the outlet of the first NO conversion device.

In another embodiment, the system is provided with a second NO conversion device similar to the first NO conversion device. In this embodiment, the second NO conversion device is placed in series with the first NO conversion device, and the patient interface is in communication with the outlet of the second conversion device. In yet another embodiment, a humidifier is placed prior to the first conversion device. In another embodiment, the humidifier is integral with the first conversion device. Optionally, an active humidifier is placed prior to the second conversion device.

Other features will become apparent from the following detailed description, taken in conjunction with the accompanying drawings, which illustrate by way of example, the features of the various embodiments.

DETAILED DESCRIPTION

Various systems and devices for generating nitric oxide (NO) are disclosed herein. Generally, NO is inhaled or otherwise delivered to a patient's lungs. Since NO is inhaled, much higher local doses can be achieved without concomitant vasodilation of the other blood vessels in the body. Accordingly, NO gas having a concentration of approximately 10 to approximately 1000 ppm (e.g., greater than 10, 40, 80, 100, 150, 200, 250, 300, 350, 400, 450, 500, 550, 600, 650, 700, 750, 800, 850, 900, 950, or 1000 ppm) may be delivered to a patient. Accordingly, high doses of NO may be used to prevent, reverse, or limit the progression of disorders which can include, but are not limited to, acute pulmonary vasoconstriction, traumatic injury, aspiration or inhalation injury, fat embolism in the lung, acidosis, inflammation of the lung, adult respiratory distress syndrome, acute pulmonary edema, acute mountain sickness, post cardiac surgery acute pulmonary hypertension, persistent pulmonary hypertension of a newborn, perinatal aspiration syndrome, haline membrane disease, acute pulmonary thromboembolism, heparin-protamine reactions, sepsis, asthma, status asthmaticus, or hypoxia. NO can also be used to treat chronic pulmonary hypertension, bronchopulmonary dysplasia, chronic pulmonary thromboembolism, idiopathic pulmonary hypertension, primary pulmonary hypertension, or chronic hypoxia.

Currently, approved devices and methods for delivering inhaled NO gas require complex and heavy equipment. NO gas is stored in heavy gas bottles with nitrogen and no traces of oxygen. NO gas is mixed with air or oxygen with specialized injectors and complex ventilators, and the mixing process is monitored with equipment having sensitive microprocessors and electronics. All this equipment is required in order to ensure that NO is not oxidized into nitrogen dioxide ($NO_2$) during the mixing process since $NO_2$ is highly toxic. However, this equipment is not conducive to use in a non-medical facility setting since the size, cost, complexity, and safety issues restrict the operation of this equipment to highly-trained professionals in a medical facility.

Figure 1:
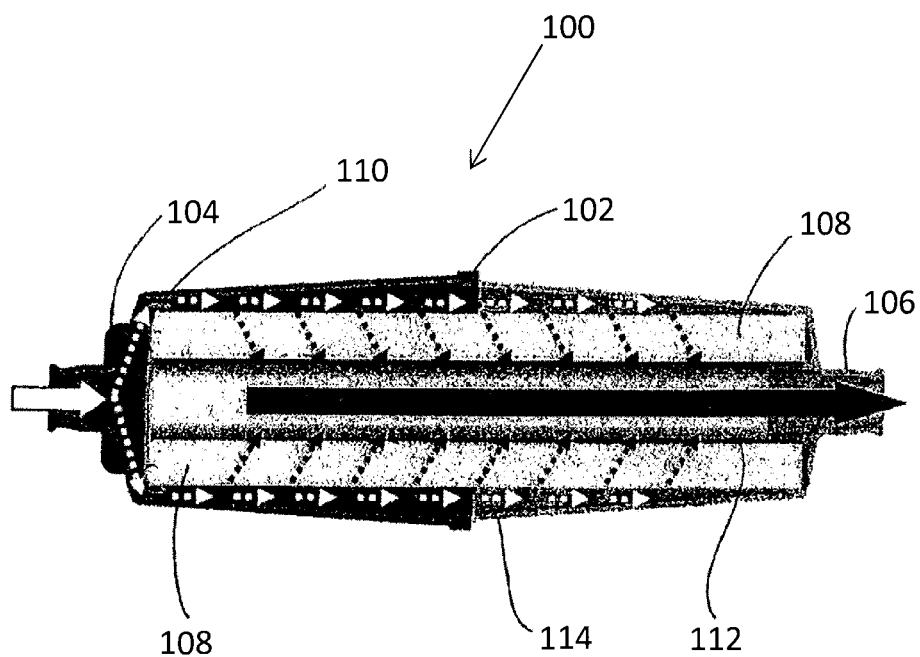
FIG. 1 is a cross-sectional view of one embodiment of a nitric oxide (NO) generating device.

In contrast, the systems and devices disclosed herein do not require heavy gas bottles, sophisticated electronics, or monitoring equipment. For example, FIG. 1 illustrates one embodiment of a device 100 that generates NO from $NO_2$. The device 100, which may be referred to as a NO generation cartridge, a GENO cartridge, a GENO cylinder, or a recuperator, includes a body 102 having an inlet 104 and an outlet 106. The inlet 104 and outlet 106 are sized to engage gas plumbing lines or directly couple to other components such as, but not limited to, gas tanks, regulators, valves, humidifiers, patient interfaces, or recuperators. Additionally, the inlet 104 and outlet 106 may include threads or specially designed fittings to engage these components.

As shown in FIG. 1, the body 102 is generally cylindrical in shape and defines a cavity that holds a solid matrix 108. According to one embodiment, the porous solid matrix 108 is a mixture of a surface-activated material such as, but not limited to, silica gel and one or more suitable thermoplastic resins that are sintered at high temperatures to form a porous solid matrix. The polymers include, but are not limited to, polyethylene, polypropylene or any thermoplastic resin that can be ground into a fine powder and the poured into a mold and sintered at high temperature to form a porous solid matrix. The thermoplastic resin, when cured, provides a rigid porous structure with the surface-activated material embedded in the pores. Additionally, the polymer may be shaped or molded into any form.

According to one embodiment, the porous solid matrix 108 is composed of at least 20% silica gel. In another embodiment, the porous solid matrix 108 includes approximately 20% to approximately 60% silica gel. In yet another embodiment, the porous solid matrix 108 is composed of 50% silica gel. As those skilled in the art will appreciate, any ratio of silica gel to thermoplastic resin is contemplated so long as the mechanical and structural strength of the porous solid matrix 108 is maintained. In one embodiment, the densities of the silica gel and the polymer are generally similar in order to achieve a uniform mixture and, ultimately, a uniform porous solid matrix 108.

As shown in FIG. 1, the porous solid matrix 108 also has a cylindrical shape having an inner bore 112. In other embodiments, the porous solid matrix may have any shape known or developed in the art. The porous solid matrix 108 is positioned within the body 102 such that a space 114 is formed between the body and the porous solid matrix. At the inlet end 104 of the body 102, a diverter 110 is positioned between the inlet and the porous solid matrix 108. The diverter 110 directs the gas flow to the outer diameter of the porous solid matrix 108 (as shown by the white arrows). Gas flow is forced through the porous solid matrix 108 whereby any $NO_2$ is converted into NO (as shown by the darkened arrows). NO gas then exits the outlet 106 of the device 100. The porous solid matrix 108 allows the device 100 to be used in any orientation (e.g., horizontally, vertically, or at any angle). Additionally, the porous solid matrix 108 provides a rigid structure suitable to withstand vibrations and abuse associated with shipping and handling.

In the device 100 shown in FIG. 1, the pressure drop across the porous solid matrix 108 is generally less than 1-2 inches of water at a gas flow rate of 40-60 liters per minute. According to one embodiment, the porous solid matrix 108 is approximately 10 inches long with an outer diameter of about 1.3 inches and an inner diameter of about 1 inch. In alternate embodiments, the porous solid matrix 108 may have different sizes and diameters based upon the intended use. For example, a portable, short-term device may have a smaller-sized, porous solid matrix as compared to a long-term device.

The body 102 of the device 100 may be made from a polymer, metal, fiberglass, glass, carbon fiber, ceramic, or other materials known or developed in the art that is not rapidly corroded or damaged by $NO_2$. Regardless of the materials used, the construction of the body 102 needs to be sealed to prevent air from entering the body. Air leakage may occur because the porous solid matrix 108 has effectively a zero pressure drop, and air can flow up around the seals of the inlet 104 or outlet 106 and into the body 102. In order to avoid air leakage into the device 100, the inside frame of the body 102 holding the solid matrix 108 has a depth that is greater than the wall thickness of the solid matrix.

Figure 2:
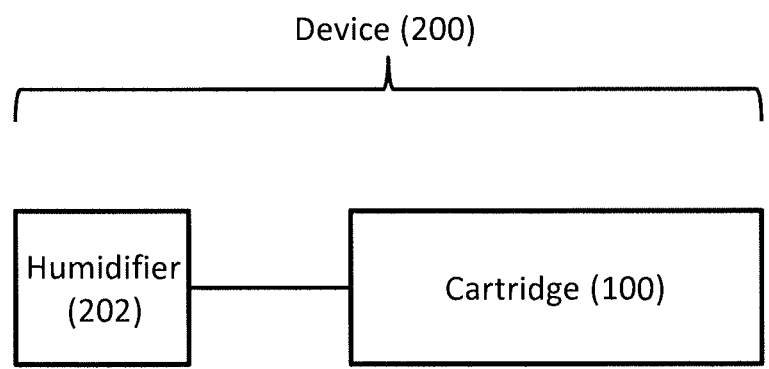
FIG. 2 is a block diagram of one embodiment of a NO generating device.

FIG. 2 illustrates another embodiment of a device 200 for converting $NO_2$ into NO. The device 200 includes a conversion cartridge 100 and a humidifier 202. The humidifier 202 enhances the lifetime of the cartridge 100 by replacing moisture in the silica gel portion of the solid matrix 108. For example, in one experiment, an unheated humidifier 202 is positioned in the flow line prior to the cartridge 100. The water temperature in the humidifier dropped from an ambient temperature of 23° C. to less than 18° C. due to evaporative cooling. The moisture from the evaporative cooling extended the life of the cartridge 100 to well over 100 hours whereas a cartridge without any humidity would have a lifespan of less than 12 hours. If a humidifier 202 is used with a cartridge 100, the humidity in the cartridge must be below the dew point. Otherwise, the presence of liquid water "drowns" the active sites on the silica gel in the device 100, thereby preventing $NO_2$ gas from interacting with the antioxidant.

As shown in FIG. 2, the humidifier 202 may be a separate device placed prior to the cartridge 100. Alternatively, the humidifier 202 and the cartridge 100 may be an integral component. In one embodiment, approximately 250 mL of water would be sufficient to maintain the moisture content in the cartridge 100 well beyond the lifetime of the porous solid matrix 108. In alternate embodiments, more or less water may be needed for larger and smaller cartridges, respectively. In other embodiments (e.g., a short-term device), a humidifier may not be necessary.

Figure 3:
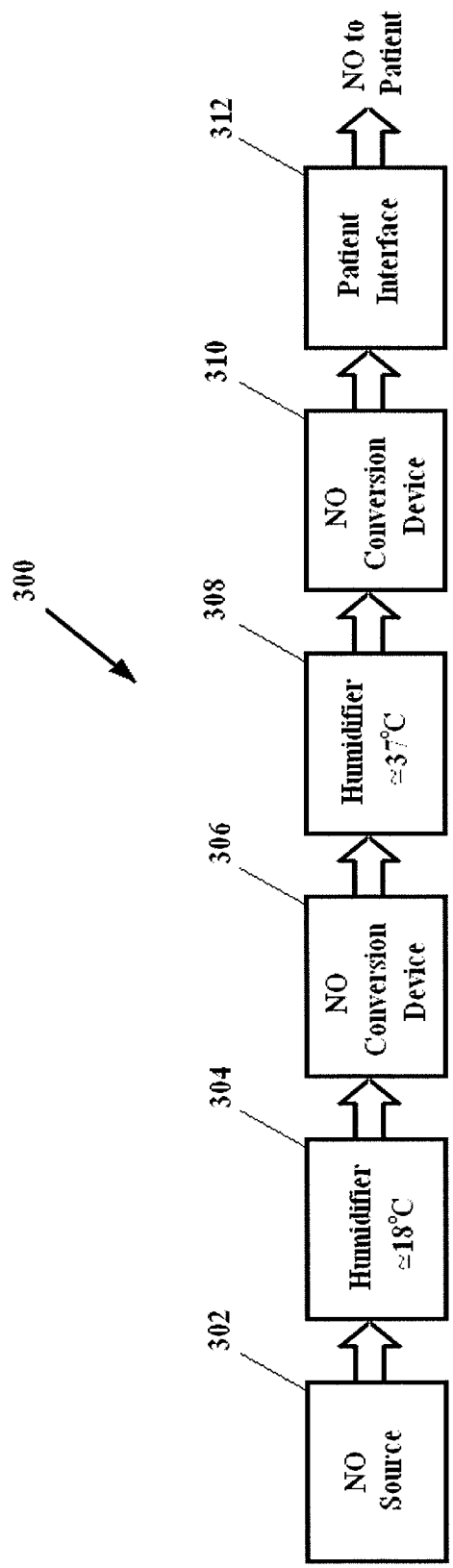
FIG. 3 is a block diagram of one embodiment of a system for delivering NO to a patient.

FIG. 3 illustrates a system 300 for delivering NO to a patient. The system 300 includes a gas source 302 for generating or containing NO. The gas source 302 may be a tank of pressurized (or non-pressurized) NO, $NO_2$, or $N_2O_4$. In those systems having a non-pressurized gas source, a pump is provided to move the gas from the gas source through the conversion cartridges 306, 310. Optionally, a humidifier 304 or 308 may be placed prior to one or more NO conversion devices 306, 310.

As shown in FIG. 3, the system 300 includes two conversion devices 306, 310. According to one embodiment, the second conversion device 310 is referred to as a recuperator. The recuperator 310 is identical to the main conversion device 306 except the recuperator is typically smaller in size and format. The recuperator 310 is generally smaller for convenience and to reduce weight and size. Nevertheless, the recuperator 310 functions the same as the main cartridge 306. In alternate embodiments of the system, the two cartridges 306, 310 may be identical (e.g., two main cartridges).

Optionally, the system 300 includes a heated humidifier 308 positioned between the conversion cartridge 310 and the patient interface 312. The patient interface 312 may be a mouth piece, nasal cannula, face mask, or fully-sealed face mask. According to one embodiment, the humidifier 308 is a heated humidifier that brings the moisture content up to a dew point of 32° C. to 37° C., thereby preventing moisture loss from the lungs.

According to one method, the solid matrix is formed by mixing silica gel with a thermoplastic resin. The mixture is then sintered at a high temperature to form a porous solid matrix and allowed to cool. After the porous solid matrix 108 is formed, the porous solid matrix is flushed with an antioxidant solution. In one embodiment, the antioxidant solution is approximately 20% ascorbic acid in water. Alternatively, ascorbic acid may be substituted with other antioxidants such as, but not limited to, alpha tocopherol or gamma tocopherol. In other embodiments, the antioxidant solution may have varying antioxidant concentrations. Dissolved gases (e.g., oxygen and air) are excluded from the antioxidant solution in order to prevent the formation of microscopic gas bubbles around the solid polymer/silica gel matrix. The gas bubbles would alter the surface chemistry and would prevent $NO_2$ from interacting with the antioxidant liquid inside the silica gel.

Once the solid matrix 108 has been flushed, the excess antioxidant solution that is not bound by the silica gel may be rinsed off in order to minimize the precipitation of excess antioxidant solution during the drying step. According to one embodiment, the porous solid matrix 108 is vacuum dried until the moisture content is reduced to approximately 30%. In alternate embodiments, the solid matrix 108 may be dried to have any moisture content ranging from approximately 1% to approximately 99%. During the drying process, precautions need to be taken to ensure that oxygen is excluded. The dried, solid matrix 108 is assembled into the body 102 and flushed with inert gas before and during the sealing process. According to one embodiment, the cartridges 100 are stored in oxygen and gas-tight containers. Oxygen is excluded from the manufacturing process and during storage in order to prevent the ascorbic acid (or other antioxidants) from slowly oxidizing to dehydro-ascorbic acid and other oxidation products during long-term storage. In another embodiment, the cartridge is dried until there is no detectable water present, and the cartridge is then sealed and packaged dry in a moisture-proof container. The dried cartridge is reconstituted into an active cartridge by exposing the cartridge to water prior to use.

The various embodiments described above are provided by way of illustration only and should not be construed to limit the claimed invention. Those skilled in the art will readily recognize various modifications and changes that may be made to the claimed invention without following the example embodiments and applications illustrated and described herein, and without departing from the true spirit and scope of the claimed invention, which is set forth in the following claims.

What is claimed:

1. A device for generating nitric oxide from nitrogen dioxide, comprising
    a body including an inlet and outlet;
    a sintered porous thermoplastic solid matrix within the body;
    a silica gel embedded in pores of the sintered porous thermoplastic solid matrix; and
    an aqueous solution of antioxidant wetting the sintered porous thermoplastic solid matrix and the silica gel,
    the inlet configured to receive a gas flow and fluidly communicate the gas flow to the outlet through the sintered porous thermoplastic solid matrix to convert nitrogen dioxide in the gas flow into nitric oxide.

2. The device of claim 1, further comprising a humidifier in communication with the inlet of the body.

3. The device of claim 1, wherein the antioxidant is ascorbic acid, alpha tocopherol, or gamma tocopherol.

4. The device of claim 1, wherein the sintered porous thermoplastic solid matrix comprises at least 20% silica gel.

5. The device of claim 1, wherein the sintered porous thermoplastic solid matrix comprises 20% to 60% silica gel.

6. The device of claim 1, wherein a density of the silica gel is the same as a density of a thermoplastic resin used to form the sintered porous thermoplastic solid matrix.

7. The device of claim 1, wherein a density of the silica gel and a density of the sintered porous thermoplastic resin are configured such that a distribution of silica gel within the porous thermoplastic solid matrix is uniform.

8. A method, comprising:
    mixing a thermoplastic resin and silica gel to form a powder mixture;
    sintering the powder mixture to form a solid matrix having silica gel embedded in pores of the solid matrix; and
    wetting the solid matrix with an aqueous solution of antioxidant.

9. The method of claim 8, further comprising:
    flowing nitrogen dioxide-containing gas over the solid matrix after wetting the solid matrix with the aqueous solution of antioxidant to form nitric oxide.

10. The method of claim 8, further comprising:
    flowing nitrogen dioxide-containing gas over the solid matrix after wetting the solid matrix with the aqueous solution of antioxidant to form nitric oxide; and
    administering the nitric oxide to a patient.

* * * * *